US009499681B2

(12) United States Patent
Ghosh-Dastidar et al.

(10) Patent No.: US 9,499,681 B2
(45) Date of Patent: Nov. 22, 2016

(54) EPOXIDIZED FATTY ACID ALKYL ESTER PLASTICIZERS AND METHODS FOR MAKING EPOXIDIZED FATTY ACID ALKYL ESTER PLASTICIZERS

(71) Applicant: Dow Global Technologies LLC, Midland, MI (US)

(72) Inventors: Abhijit Ghosh-Dastidar, East Brunswick, NJ (US); Saurabh Kaujalgikar, Pune (IN); Bharat I. Chaudhary, Princeton, NJ (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/429,112

(22) PCT Filed: Nov. 12, 2012

(86) PCT No.: PCT/IN2012/000746
§ 371 (c)(1),
(2) Date: Mar. 18, 2015

(87) PCT Pub. No.: WO2014/072987
PCT Pub. Date: May 15, 2014

(65) Prior Publication Data
US 2015/0337112 A1 Nov. 26, 2015

(51) Int. Cl.
| | |
|---|---|
| *C08K 5/00* | (2006.01) |
| *C08K 5/101* | (2006.01) |
| *C07C 53/126* | (2006.01) |
| *C07C 67/03* | (2006.01) |
| *C07D 303/04* | (2006.01) |
| *C08K 5/1515* | (2006.01) |

(52) U.S. Cl.
CPC ........... *C08K 5/0016* (2013.01); *C07C 53/126* (2013.01); *C07C 67/03* (2013.01); *C07D 303/04* (2013.01); *C08K 5/101* (2013.01); *C08K 5/1515* (2013.01)

(58) Field of Classification Search
CPC .................. C08K 5/101; C08K 5/1515; C07D 303/04; C07C 53/126; C07C 67/03
See application file for complete search history.

(56) References Cited

U.S. PATENT DOCUMENTS

| | | | |
|---|---|---|---|
| 2,397,592 | A | 4/1946 | Blades |
| 2,403,215 | A | 7/1946 | Foster |
| 2,458,484 | A | 1/1949 | Terry et al. |
| 2,500,918 | A | 3/1950 | Rueter et al. |
| 2,618,622 | A | 11/1952 | Grummit et al. |
| 2,666,752 | A | 1/1954 | Grummit et al. |
| 3,138,566 | A | 6/1964 | Arnold |
| 3,254,097 | A | 5/1966 | Darrow |
| 3,377,304 | A * | 4/1968 | Kuester ................... C08K 5/101 524/114 |
| 3,409,580 | A | 11/1968 | Alzner |
| 3,451,958 | A | 6/1969 | Riedeman et al. |
| 3,639,318 | A | 2/1972 | Tijunelis et al. |
| 3,668,091 | A | 6/1972 | French et al. |
| 3,712,875 | A | 1/1973 | Tijunelis |
| 3,778,465 | A | 12/1973 | Barnstorf |
| 3,780,140 | A | 12/1973 | Hammer |
| 3,868,341 | A | 2/1975 | Sauer et al. |
| 3,872,187 | A | 3/1975 | Fath |
| 3,891,694 | A | 6/1975 | Mills et al. |
| 4,083,816 | A | 4/1978 | Frankel et al. |
| 4,346,145 | A | 8/1982 | Choi et al. |
| 4,421,886 | A | 12/1983 | Worschech et al. |
| 4,426,477 | A | 1/1984 | Yasumatsu et al. |
| 4,556,694 | A | 12/1985 | Wallace |
| 4,605,694 | A | 8/1986 | Walker |
| 4,612,192 | A | 9/1986 | Scheuffgen et al. |
| 4,613,533 | A | 9/1986 | Loomis et al. |
| 4,627,993 | A | 12/1986 | Loomis |
| 4,670,494 | A | 6/1987 | Semenza, Jr. |
| 4,857,600 | A | 8/1989 | Gross et al. |
| 5,225,108 | A | 7/1993 | Bae et al. |
| 5,227,417 | A | 7/1993 | Kroushl, III |
| 5,246,783 | A | 9/1993 | Spenadel et al. |

(Continued)

FOREIGN PATENT DOCUMENTS

| | | |
|---|---|---|
| CA | 1188445 A1 | 6/1985 |
| CN | 1341681 | 3/2002 |

(Continued)

OTHER PUBLICATIONS

European Commission Opinion on Medical Devices Containing DEHP Plasticized PVC; Neonates and Other Groups Possibly at Risk from DEHP Toxicity, 2002, p. 1-34.*
PCT/IN2012/000745, International Preliminary Report on Patentability, Issued May 12, 2015.
PCT/US2013/039841, International Search Report and Written Opinion, Mailed Mar. 27, 2014.
PCT/US2013/039841, International Preliminary Report on Patentability, Issued Dec. 21, 2014.
PCT/IN2012/00688, International Search Report and Written Opinion, Mailed Jun. 18, 2013.
PCT/IN2012/00688, International Preliminary Report on Patentability, Issued Apr. 30, 2015.
PCT/IN2012/000746 International Search Report and Written Opinion, Mailed May 31, 2013.

(Continued)

*Primary Examiner* — Robert Jones, Jr.

(57) ABSTRACT

Epoxidized fatty acid alkyl esters and methods for making epoxidized fatty acid alkyl esters. Such epoxidized fatty acid alkyl esters can be prepared by epoxidizing fatty acid alkyl esters with an acid and a peroxide. Epoxidation can be performed under controlled reaction conditions to provide epoxidized fatty acid alkyl esters having an iodine value in the range of from 4 to 15 g $I_2$/100 g of epoxidized fatty acid alkyl esters. Epoxidized fatty acid alkyl esters can be employed in plasticizer compositions, either alone or in combination with other plasticizers, such as epoxidized natural oils. Such plasticizers in turn may be used in the formation of polymeric compositions.

6 Claims, No Drawings

(56) References Cited

U.S. PATENT DOCUMENTS

| | | |
|---|---|---|
| 5,270,366 A | 12/1993 | Hein |
| 5,278,236 A | 1/1994 | Case et al. |
| 5,430,108 A | 7/1995 | Schlosberg et al. |
| 5,454,806 A | 10/1995 | Shinonome |
| 5,464,903 A | 11/1995 | Hofmann |
| 5,466,267 A | 11/1995 | Baillargeon et al. |
| 5,575,965 A | 11/1996 | Caronia et al. |
| 5,736,605 A | 4/1998 | Oshima |
| 5,756,570 A | 5/1998 | Hoch et al. |
| 5,886,072 A | 3/1999 | Linsky et al. |
| 6,063,846 A | 5/2000 | Weng et al. |
| 6,114,425 A | 9/2000 | Day et al. |
| 6,274,750 B1 | 8/2001 | Sato et al. |
| 6,417,260 B1 | 7/2002 | Weng et al. |
| 6,437,170 B1 | 8/2002 | Thil et al. |
| 6,451,958 B1 | 9/2002 | Fan et al. |
| 6,495,033 B1 | 12/2002 | Talboom |
| 6,496,629 B2 | 12/2002 | Ma et al. |
| 6,608,142 B1 | 8/2003 | Weng et al. |
| 6,706,815 B2 | 3/2004 | Marchand et al. |
| 6,714,707 B2 | 3/2004 | Rossi et al. |
| 6,734,241 B1 | 5/2004 | Nielsen et al. |
| 6,797,753 B2 | 9/2004 | Benecke et al. |
| 6,849,694 B2 | 2/2005 | Hata |
| 6,949,597 B2 | 9/2005 | Nielsen et al. |
| 7,700,675 B2 | 4/2010 | Bueno de Almeida et al. |
| 2002/0013396 A1 | 1/2002 | Benecke et al. |
| 2004/0122159 A1 | 6/2004 | Mhetar et al. |
| 2005/0090590 A1 | 4/2005 | Nielsen et al. |
| 2005/0203230 A1 | 9/2005 | Kadakia et al. |
| 2006/0025544 A1 | 2/2006 | Koube et al. |
| 2006/0276575 A1 | 12/2006 | Hamaguchi et al. |
| 2007/0100049 A1 | 5/2007 | Ishizuka |
| 2007/0135562 A1 | 6/2007 | Freese et al. |
| 2008/0200595 A1* | 8/2008 | Hinault ............ C08K 5/101 524/273 |
| 2008/0227993 A1 | 9/2008 | Zuckerman |
| 2009/0149585 A1 | 6/2009 | De Quadros Junior et al. |
| 2009/0149586 A1 | 6/2009 | De Quadros Junior et al. |
| 2009/0312478 A1 | 12/2009 | Hasegawa et al. |
| 2010/0010127 A1 | 1/2010 | Barki et al. |
| 2010/0256278 A1 | 10/2010 | Harada et al. |
| 2011/0076502 A1 | 3/2011 | Chaudhary et al. |
| 2011/0272174 A1 | 11/2011 | Chaudhary |
| 2012/0181058 A1* | 7/2012 | Chaudhary ......... C08K 5/0091 174/110 V |
| 2012/0289727 A1* | 11/2012 | Cordeiro ............ C07C 67/03 554/170 |
| 2013/0005937 A1 | 1/2013 | Cramail et al. |
| 2013/0123408 A1* | 5/2013 | Maurer ............... C11C 3/00 524/313 |

FOREIGN PATENT DOCUMENTS

| | | |
|---|---|---|
| CN | 101070510 | 11/2007 |
| CN | 101108982 A | 1/2008 |
| CN | 101445495 A | 6/2009 |
| CN | 101591588 A | 12/2009 |
| CN | 101824193 A | 9/2010 |
| CN | 101891713 A | 11/2010 |
| CN | 101914219 A | 12/2010 |
| EP | 0192961 A1 | 9/1986 |
| EP | 0358179 A2 | 3/1990 |
| EP | 0364717 A1 | 4/1990 |
| EP | 0 393 813 A1 | 10/1990 |
| EP | 0473915 A1 | 3/1992 |
| EP | 0565984 A1 | 10/1993 |
| EP | 0986606 A1 | 3/2000 |
| EP | 1218443 A1 | 7/2002 |
| EP | 1361039 A1 | 11/2003 |
| EP | 1624014 A1 | 2/2006 |
| EP | 2070977 A2 | 6/2009 |
| EP | 2245089 A1 | 11/2010 |
| FR | 1437722 A | 5/1966 |
| GB | 102292 A | 11/1916 |
| GB | 499931 A | 1/1939 |
| GB | 790314 A | 2/1958 |
| GB | 910543 A | 11/1962 |
| GB | 934689 A | 8/1963 |
| GB | 1020866 A | 2/1966 |
| GB | 1102506 A | 2/1968 |
| GB | 1341623 A | 12/1973 |
| GB | 2155021 A | 9/1985 |
| JP | S44-007131 | 3/1969 |
| JP | S61-016950 | 1/1986 |
| JP | 04-059851 B2 | 2/1992 |
| JP | H04-085354 | 3/1992 |
| JP | H04-261452 A | 9/1992 |
| JP | 2000-319468 A | 11/2000 |
| JP | 2003-064233 A | 3/2003 |
| JP | 2003-297149 A | 10/2003 |
| JP | 2004311064 A | 11/2004 |
| JP | 2010-042669 A | 2/2010 |
| WO | 9730115 A1 | 8/1997 |
| WO | 0114466 A1 | 3/2001 |
| WO | 0198404 A2 | 12/2001 |
| WO | 2004052977 A1 | 6/2004 |
| WO | 2007006489 A1 | 1/2007 |
| WO | 2008081330 A1 | 7/2008 |
| WO | 2008081332 A1 | 7/2008 |
| WO | 2008122364 A1 | 10/2008 |
| WO | 2009102877 A1 | 8/2009 |
| WO | 2011/041380 A1 | 4/2011 |
| WO | 2011/041388 A1 | 4/2011 |
| WO | 2011041372 A1 | 4/2011 |
| WO | WO2011041396 * | 4/2011 |
| WO | WO2011072346 * | 6/2011 |
| WO | WO2012015997 * | 2/2012 |
| WO | 2013003225 A2 | 1/2013 |

OTHER PUBLICATIONS

PCT/IN2012/000746, International Preliminary Report on Patentability, Issued May 12, 2015.

PCT/US2013/039840 International Search Report and Written Opinion, Mailed Jul. 11, 2013.

PCT/US2013/039840, International Preliminary Report on Patentability, Issued Dec. 31, 2014.

PCT/US2014/020556 International Search Report and Written Opinion, Mailed Jun. 25, 2014.

PCT/US2010/050654, International Preliminary Report on Patentability, Issued Mar. 31, 2012.

PCT/US2010/050676, International Preliminary Report on Patentability, Issued Mar. 31, 2012.

PCT/US2011/045653, International Preliminary Report on Patentability, Issued Jan. 28, 2013.

PCT/US2012/043740, International Preliminary Report on Patentability, Issued Jan. 7, 2014.

PCT/US2012/055070, International Preliminary Report on Patentability, Issued Apr. 1, 2014.

PCT/US2010/050669, International Preliminary Report on Patentability, Issued Apr. 11, 2012.

PCT/US2011/035143, International Preliminary Report on Patentability, Issued Nov. 10, 2012.

http://en.wikipedia.org/wiki/Chlorine.

http://en.wikipedia.org/wiki/Bleaching_of_wood_pulp.

TCI America, Online Catalog: Tributyrin; http://web.archive.org/web/20080511154307/http://www.tciamerica.com/.

PCT/ US2009/033935, International Preliminary Report on Patentability, MailedAug. 26, 2010.

PCT/US2009/033935 International Search Report and Written Opinion, Mailed Mailed May 18, 2009.

PCT/US2010/050654 International Search Report and Written Opinion Mailed Nov. 9, 2010.

PCT/US2010/050676 International Search Report and Written Opinion Mailed Jan. 12, 2011.

PCT/US2010/050690 International Preliminary Report on Patentability, Mailed Jan. 12, 2012

(56) References Cited

OTHER PUBLICATIONS

PCT/US2010/050690 International Search Report and Written Opinion, Mailed Aug. 2, 2011.
PCT/US2010/050699 International Search Report and Written Opinion, Mailed Nov. 8, 2010.
PCT/US2011/035143 International Search Report and Written Opinion, Mailed Aug. 26, 2011.
Barnicoat, C.R. 1945. Reactions and properties of annatto as a cheese colour. Part II. J. Dairy Res. 14: 59-63.
Bizzari, S.N. et al (2003), Plasticizers. CEH Marketing Research Report, 38-64, Retrieved from http://www.sriconsulting.com.
Campanella A. et al.; High Yield Epoxidation of Fatty Acid Methyl Esters with Performic Acid Generated in Situ; Chemical Engineering Journal, 144 (2008) 466-475 (Elsevier B.V.).
Chuanshang Cai, et al.; Studies on the Kinetics of In Situ Epoxidation of Vegetable Oils; Eur. J. Lipid Sci. Technol., 2008, 110, 341-346 (Wiley-VCH GmbH & Co. KGaA, Weinheim).
Corrigan, Brian Oil purification, filtration and reclamation, Iron Age (1947) 159(14).
Danisco, Grindsted Soft-n-Safe brochure (date unknown).
Du G., et al., Catalytic Epoxidation of Methyl Linoleate, JAOCS, vol. 81, No. 4 (2004).
Freedman, F., Butterfield, R., and Pryde, E.H. Transesterification Kinetics of Soybean Oil. JAOCS, 63(10) p. 1375 (1986).
Gan, L. H., et al (1994) Epozidized esters of palm olein as plasticizers for poly (vinyl chloride). European Polymer Journal, 31(8), 719-724.
Greenspan, F. P. et al (1953) Epoxy fatty acid ester plasticizers. Indstrial and Engineering Chemistry, 445(12), 2722-2726.
Greenspan, F.P. et al (1956), Epoxy fatty acid ester plasticizers. Preparartion and properties, The Journal of the American Oil Chemists Society, 33, 391-394.
Grummitt O. and Fleming H. Acetylated Castor Oil Industrial and Engineering Chemistry, vol. 37, No. 5, May 1945, pp. 485-491.
Haas, Michael J. Improving the Economics of biodiesel production through the use of low value lipids as feedstocks: vegetable oil soapstock, Fuel Processing Technology 86 p. 1087-96 (2005).
Jensen, R.G. Purification of Triglycerides with an Aluminca Column, Lipids, 451-452 (1966).
Morgenstern, B. "Epoxidized Fatty Acid Esters as Plasticizers for PVC" dated Apr. 22, 2005.
Morgenstern, B. Epoxidized Fatty Acid Esters as Plasticizers for PVC, presented at the 7th Freiberg Polymer Conference, Apr. 21 and 22, 2005.
Morgenstern, B. Use of Modified Fatty Acid Esters as Plasticizers for PVC, dated Sep. 12, 2003.
Opposition to patent EP2245089, Dated Jan. 9, 2013.
Orellana-Coca et al., Lipase Mediated Simultaneious Esterification and Epoxidation of Oleic Acid for the Production of Alkylepoxystearates. Journal of Molecular Catalysis B: Enzymatic 44 (2007) 133-137.
Stuart, A et al., Polym. Bull. (2010) 65:589-598.
Rehberg, C. et. Al. Plasticizers from Lactic Esters and Biabasic Acids Ind. Eng. Chem., 1952, 44 (9), pp. 2191-2195.
Santacesaria E. et al.; A Biphasic Model Describing Soybean Oil Epoxidation with H2O2 in a Fed-Batch Reactor; Chemical Engineering Journal, vol. 173, Issue 1, Sep. 1, 2011, pp. 198-209 (Elsevier B.V.).
Senžana S. et al.; Kinetics of In Situ Epoxidation of Soybean Oil in Bulk Catalyzed by Ion Exchange Resin; Journal of the American Oil Chemists' Society, vol. 78, No. 7 (2001) 725-731 (AOCS Press).
Sheehan, J et al. "A Look Back at the U.S. Department of Energy's Aquatic Species Program: Biodiesel from Algae", National Renewable Energy Laboratory, Colorado, Jul. 1998, pp. 1-294.
Taylor, D. R. Proceedings of the World Conference on oilseed technology and utilization, Adsorptive Purification, American Oil Chemists Society, Champaing, 1992, p. 152-165.
Tekin A., and Hammond E. Factors Affecting the Electrical Resistivity of Soybean Oil, JAOCS, vol. 75(6) 1998.
XP002657062 Vertellus Performance Materials Inc.; Flexricin P-8 Technical Data Sheet, Nov. 2006.
XP002669860, Thomson Scientific, Mar. 13, 2009, London, GB.
PCT/US2011/041557 International Preliminary Report on Patentability, Mailed Aug. 31, 2012.
PCT/US2011/041557 International Search Report and Written Opinion Mailed Sep. 5, 2011.
PCT/US2011/045653 International Search Report and Written Opinion, Mailed Oct. 7, 2011.
PCT/US2012/043740 International Search Report and Written Opinion, Mailed Jan. 23, 2013.
PCT/US2012/055070 International Search Report and Written Opinion, Mailed Dec. 3, 2012.
PCT/US2013/023362 International Search Report and Written Opinion, Mailed Mar. 28, 2013.
PCT/US2013/023362, International Preliminary Report on Patentability, Issued Aug. 12, 2014.
PCT/US2011/059166 International Search Report and Written Opinion, Mailed Feb. 29, 2012.
PCT/US2011/059166, International Preliminary Report on Patentability, Issued May 7, 2013.
PCT/IN2012/000745 International Search Report and Written Opinion, Mailed Aug. 29, 2013.

* cited by examiner

EPOXIDIZED FATTY ACID ALKYL ESTER PLASTICIZERS AND METHODS FOR MAKING EPOXIDIZED FATTY ACID ALKYL ESTER PLASTICIZERS

FIELD

Various embodiments of the present invention relate to methods for making epoxidized fatty acid alkyl esters. Such epoxidized fatty acid alkyl esters may be employed as plasticizers or in plasticizer compositions.

INTRODUCTION

Plasticizers are compounds or mixtures of compounds that, when added to polymer resins, can lower one or more of the modulus and tensile strength, and increase one or more of flexibility, elongation, impact strength, and tear strength of the resin (typically a thermoplastic polymer) to which they are added. A plasticizer may also lower the melting point of the polymer resin, which lowers the glass transition temperature and enhances processability of the polymer resin.

Phthalic acid diesters (also known as "phthalates") are commonly used as plasticizers in many flexible polymer products, such as polymer products formed from polyvinyl chloride ("PVC") and other vinyl polymers. Examples of phthalate plasticizers include diisononyl phthalate, diallyl phthalate, di-2-ethylhexyl-phthalate, dioctyl phthalate, and diisodecyl phthalate. Other plasticizers used for high temperature applications are trimellitates and adipic polyesters.

Phthalate plasticizers have recently come under intense scrutiny by public interest groups concerned about the negative environmental impact of phthalates and potential adverse health effects in humans exposed to phthalates. Accordingly, plasticizers that minimize or eliminate the use of phthalates are needed. Although advancements have been made, improvements in such plasticizers are still desired.

SUMMARY

One embodiment is a plasticizer composition comprising: epoxidized fatty acid alkyl esters, wherein said epoxidized fatty acid alkyl esters have an iodine value in the range of from 4 to 15 g $I_2$/100 g of epoxidized fatty acid alkyl esters.

Another embodiment is a process for producing epoxidized fatty acid alkyl esters, said process comprising: epoxidizing fatty acid alkyl esters via controlled epoxidation by contact with an acid and an aqueous peroxide solution to form epoxidized fatty acid alkyl esters, wherein said controlled epoxidation comprises selecting a reaction temperature, a reaction time, an aqueous peroxide solution concentration, and a peroxide solution feed rate to cause said epoxidized fatty acid alkyl esters to retain sufficient unsaturation to present an iodine value in the range of from 4 to 15 g $I_2$/100 g of epoxidized fatty acid alkyl esters.

DETAILED DESCRIPTION

Various embodiments of the present invention concern methods for preparing epoxidized fatty acid alkyl esters ("eFAAE") from esterified natural oils. Such eFAAEs can be employed as a plasticizer alone or in combination with an epoxidized natural oil ("eNO"). Plasticizers comprising eFAAE and optionally eNO can be employed with a variety of polymeric resins and in making various articles of manufacture.

Preparing Epoxidized Fatty Acid Alkyl Esters

The eFAAE can be prepared by epoxidation of an esterified (e.g., transesterified) natural oil. Thus, in one or more embodiments, the eFAAE can be prepared by first subjecting a natural oil to esterification (e.g., transesterification), thereby producing fatty acid alkyl esters. The term "natural oil" denotes an oil comprising fatty acid triglycerides and is derived from a microbe (algae, bacteria), a plant/vegetable, and/or a seed. In an embodiment, the natural oil includes genetically-modified natural oil. In another embodiment, the natural oil excludes petroleum-derived oil. Non-limiting examples of suitable natural oils include algae oil, beef tallow oil, canola oil, castor oil, corn oil, fish oil, linseed oil, palm oil, rapeseed oil, safflower oil, soybean oil, sunflower oil, tall oil, tung oil, and combinations of two or more thereof. In an embodiment, the natural oil is selected from the group consisting of soybean oil, canola oil, linseed oil, and combinations thereof. In an embodiment, the natural oil is soybean oil. In an embodiment, the natural oil has a linolenic acid content of greater than 5 weight percent ("wt %").

In an embodiment, esterification of the natural oil is performed via transesterification. Transesterification can be performed using any conventional or hereafter discovered techniques. In an embodiment, the natural oil is transesterified via contact with an alcohol under transesterification conditions with either an acid or base catalyst. Glycerol byproduct is removed from the reaction products due to insolubility. The alcohol employed for transesterification is selected based on the desired alkyl substituent of the fatty acid alkyl esters. Alcohols suitable for use in transesterification include $C_1$ to $C_8$ monohydric linear alcohols, such as methanol, ethanol, propanol, and butanol, or $C_3$ to $C_8$ branched alcohols, such as isopropanol, isobutanol, and 2-ethylhexanol. In an embodiment, the alcohol is methanol, such that the resultant fatty acid alkyl esters are fatty acid methyl esters.

In an embodiment, the fatty acid alkyl esters have the structure: $R^1$—C(=O)O—$R^2$, where $R^1$ is a linear or branched $C_1$ to $C_8$ alkyl group, and $R^2$ represents one or more of saturated, mono-unsaturated, and polyunsaturated $C_{12}$ to $C_{22}$ fatty acid chains.

A catalyst may also be employed for esterification (e.g., transesterification). Catalysts suitable for use in esterification include homogeneous alkali catalysts, including metal alkoxides such as sodium methoxide, potassium methoxide, and sodium ethoxide, or metal hydroxides such as potassium hydroxide, sodium hydroxide, or supported solid alkali catalysts. Other classes of catalysts that may also be employed include acids, acidic resins, double metal cyanide catalysts, enzymes, super acids, super bases, and metal salts. The catalyst can be in homogeneous or heterogeneous form. In an embodiment, the catalyst employed for transesterification is sodium methoxide solution in methanol.

Commercially available FAAEs may be employed in various embodiments. Examples of suitable commercially available FAAEs include SOYCLEAR™ 1500 and SOY-GOLD™ 1100 (fatty acid methyl esters from soybean oil, available from AG Environmental Products, Inc.); CANOLAGOLD™ 110 (fatty acid methyl esters from canola oil, available from AG Environmental Products, Inc.); and SE-1885 and SE-1885D (fatty acid methyl esters from soybean oil, available from Felda Iffco, Inc.).

The fatty acid alkyl esters are then epoxidized via contact with an acid and an aqueous peroxide solution to thereby produce an epoxidized reaction mixture comprising epoxidized fatty acid alkyl esters, residual acid, residual peroxide, and water. Suitable peroxides for use in epoxidizing the natural oil include aqueous solutions of hydrogen peroxide, peroxycarboxylic acids, alkyl hydroperoxides, and tertiary hydroperoxides. In an embodiment, the peroxide employed is an aqueous solution of hydrogen peroxide.

Suitable acids for use in epoxidizing the fatty acid alkyl esters include carboxylic acids, such as formic acid and acetic acid; and peroxycarboxylic acids, such as performic acid and peracetic acid. In an embodiment, a peroxycarboxylic acid is employed, acting as both the acid and the peroxide. Catalysts such as mineral acids (e.g., sulfuric acid) and heterogeneous acid resins (e.g., Amberlite™ IR 120H, available from Rohm & Haas) may optionally be employed in the presence of the acid. In an embodiment, the acid employed for epoxidation is formic acid.

In one or more embodiments, the epoxidation reaction is controlled so as to produce eFAAEs having an iodine value in the range of from 4 to 15 grams of iodine per 100 grams of epoxidized fatty acid alkyl esters ("g $I_2$/100 g"), in the range of from 4 to 10 g $I_2$/100 g, in the range of from 7 to 10 g $I_2$/100 g, or in the range of from 8 to 10 g $I_2$/100 g. Iodine value is determined according to the American Oil Chemists' Society ("AOCS") recommended practice Cd 1-25. Additionally, the controlled epoxidation reaction conditions can be selected so as to produce eFAAEs having an oxirane oxygen content of at least 6 wt %, or at least 6.5 wt %, based on the entire weight of the eFAAEs. In various embodiments, the eFAAEs can have an oxirane oxygen content up to 8 wt %, or 7.5 wt %, based on the entire weight of the eFAAEs. Oxirane oxygen content is determined according to AOCS recommended practice Cd 9-57.

Controlled epoxidation comprises selecting a combination of reaction temperature, reaction time, aqueous peroxide solution concentration, molar ratio of peroxide-to-carbon/carbon double bonds, and peroxide solution feed rate to achieve the desired iodine value and/or oxirane oxygen content. In an embodiment, the epoxidation reaction temperature employed can be maintained in the range of from 20 to 60° C., in the range of from 30 to 50° C., or in the range of from 40 to 50° C. In various embodiments, the aqueous peroxide solution employed can have a concentration of less than 50 volume percent ("vol %"), less than 40 vol %, in the range of from 20 to 40 vol %, in the range of from 25 to 35 vol %, or of 30 vol %. In one or more embodiments, the molar ratio of peroxide-to-carbon/carbon double bounds in the FAAE can be from 1.5 to 2, from 1.7 to 2, or 2. In an embodiment, the peroxide solution feed rate can range from 0.2 to 2 grams of peroxide solution per gram of fatty acid alkyl esters per hour. In another embodiment, the peroxide solution feed rate can range from 0.3 to 4 moles of peroxide solution per molar equivalent of carbon-carbon double bonds in the fatty acid alkyl esters per hour. Regardless of which measurement is employed for determining the peroxide solution feed rate, in an embodiment, the peroxide solution feed rate can be controlled so that the epoxidation reaction temperature does not exceed the desired maximum temperature described above. In an embodiment, the peroxide feed rate can be controlled so as to prevent the epoxidation reaction temperature from exceeding 60° C., 50° C., or 40° C.

In some embodiments, the reaction conditions chosen to maintain the above-described iodine value may cause decreased oxirane oxygen content. In order to achieve the desired oxirane oxygen content (e.g., at least 6 or at least 6.5 wt %), a longer-than-conventional reaction time may be employed. In various embodiments, the reaction time employed for controlled epoxidation can be greater than 6 hours, in the range of from 7 to 20 hours, in the range of from 8 to 15 hours, or in the range of from 10 to 12 hours.

Though not wishing to be bound by theory, it was surprisingly found that maintaining an iodine value of at least 4 produces eFAAE having low concentrations of hydrophilic impurities compared to conventional eFAAE. The term "hydrophilic impurities" denotes epoxidized fatty acid ester compounds containing hydroxyl groups formed from degraded epoxy rings on the fatty acid chain. In an embodiment, the eFAAE can have a hydrophilic impurities content of less than 0.8 wt %, less than 0.7 wt %, less than 0.6 wt %, less than 0.5 wt %, less than 0.4 wt %, less than 0.3 wt %, less than 0.2 wt %, or less than 0.1 wt % based on the entire weight of the eFAAE. Hydrophilic impurities content is determined by high performance liquid chromatography ("HPLC") according to the test method described in the following Examples.

Following epoxidation, the residual acid, peroxide, and water is removed from the epoxidized reaction mixture via layer separation and neutralization. Layer separation involves separation of an aqueous layer, which contains water, acids, peroxide, and possible traces of oil and esters, from an organic layer containing the eFAAE. To accomplish layer separation, the reaction mixture is allowed to settle and separate into two layers by density difference, and the bottom aqueous layer is disposed of while the top organic layer is processed further to obtain the desired product.

Following layer separation, the residual acid can be neutralized, such as by contact with a sodium/bicarbonate solution. Thereafter, the organic layer can be washed one or more times with water. In an embodiment, the organic layer is washed repeatedly until it is neutral (having a pH of about 7). Thereafter, the washed mixture can be subjected to layer separation again, followed by vacuum distillation of the top organic layer to remove residual water.

Plasticizer

The present disclosure provides a plasticizer composition comprising eFAAE, prepared as described above. Optionally, the plasticizer composition can further include other types of plasticizers, such as an eNO. Suitable epoxidized natural oils include epoxidized animal and vegetable oils, such as epoxidized soybean oil ("eSO"), epoxidized corn oil, epoxidized sunflower oil, epoxidized palm oil, epoxidized linseed oil, epoxidized canola oil, epoxidized rapeseed oil, epoxidized safflower oil, epoxidized tall oil, epoxidized tung oil, epoxidized fish oil, epoxidized beef tallow oil, epoxidized castor oil, or combinations thereof. In an embodiment, the present plasticizer is a phthalate-free plasticizer, or is otherwise void or substantially void of phthalate.

When both eFAAE and eNO are present, the plasticizer composition can contain relative amounts of eFAAE (e.g., eFAME) to eNO (e.g., eSO) in a weight ratio in the range of from greater than (">") 0: less than ("<") 100 to <100:>0, more typically from 10:90 to 90:10, more typically from 20:80 to 80:20, and even more typically from 30:70 to 70:30. In another embodiment, the plasticizer composition comprises from 20 to less than 100 wt % eFAAE and from greater than 0 to 80 wt % eSO. Weight ratios and weight percents are based on total weight of the plasticizer composition. In various embodiments, the plasticizer composition consists of or consists essentially of eFAAE and eNO.

Polymeric Composition

The present disclosure provides a polymeric composition. In an embodiment, a polymeric composition is provided which includes a polymeric resin and the present plasticizer as disclosed above.

Non-limiting examples of suitable polymeric resins include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, EPDM rubber, propylene-based polymers, ethylene-based polymers, and vinyl chloride resins. The term, "propylene-based polymer," as used herein, is a polymer that comprises a majority weight percent polymerized propylene monomer (based on the total amount of polymerizable monomers), and optionally may comprise at least one polymerized comonomer. The term, "ethylene-based polymer," as used herein, is a polymer that comprises a majority weight percent polymerized ethylene monomer (based on the total weight of polymerizable monomers), and optionally may comprise at least one polymerized comonomer.

The term "vinyl chloride resin," as used herein, is a vinyl chloride polymer, such as polyvinyl chloride ("PVC"), or a vinyl chloride copolymer such as vinyl chloride/vinyl acetate copolymer, vinyl chloride/vinylidene chloride copolymer, vinyl chloride/ethylene copolymer or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer.

In an embodiment, the polymeric resin is PVC.

In an embodiment, the polymeric composition includes from 25 wt % to 90 wt % PVC, from 5 wt % to 35 wt % eFAAE, from 0 wt % to 35 wt % eNO, and from 0 wt % to 35 wt % filler.

Additives

The polymeric composition may include one or more of the following optional additives: a filler, an antimicrobial agent, a biocide, a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition includes PVC, the present plasticizer, a filler (calcium carbonate, clays, silica, and any combination thereof), metal soap stabilizers (zinc stearate or mixed metal soap stabilizers containing Ca, Zn, Mg, Sn, and any combination thereof), a phenolic or related antioxidant, and a processing aid.

Articles of Manufacture

Articles of manufacture can be prepared that comprise the above-described polymeric compositions. Such articles of manufacture can include those designed for use in the medical or food industries, particularly those articles that may frequently come into contact with water and where water-leachable compounds are a concern. Exemplary articles of manufacture include blood bags, intravenous bags, saline solution bags, syringes, intravenous tubing, nasogastric tubing, catheter tubing, drainage tubing, examination gloves, oxygen masks, orthodontic retainers, artificial skin, and food packaging (e.g., packaging for various beverages, meats, and frozen vegetables).

TEST METHODS

Hydrophilic Impurities Measurement

Quantify the amount of water-leachable (i.e., hydrophilic) impurities using HPLC with an evaporative light-scattering detector ("ELSD"). The method is as follows:

1) Add 0.04 g of eFAME (liquid) to 8 g of deionized water;
2) Heat the sample in an oven at 40° C. for 24 hours;
3) Remove 1 mL of the sample from the bottom of the vial;
4) Perform HPLC-ELSD for each sample.

| HPLC setup: | |
|---|---|
| Mobile phase: | $H_2O$/Acetonitrile (A/B) |
| Column: | ODS C-18; 2.1 × 100 mm, 3 µm particle size |
| Gradient: | Time (min)    % B (Acetonitrile) |
| | 0.0              88 |
| | 1.8              88 |
| | 2.6             100 |
| | 7.0             100 |
| | 9.0              88 |
| | 11.0             88 |
| Flow: | 0.30 ml/min. |
| Oven Temp.: | 70° C. |
| Injection: | 2 µl |
| Run Time: | 11 min. |
| Post Time: | 2 min. |
| ELSD setup: | |
| Instrument: | Alltech 3300 ELSD |
| Tube Temp.: | 70° C. |
| Gas Flow: | 1.80 SLPM |
| Gain: | 1.0 |
| $N_2$ regulator: | 60 psig |

Oxirane Oxygen Content

Determine oxirane oxygen content according to AOCS Cd 9-57.

Iodine Value

Determine iodine value according to AOCS Cd 1-25.

EXAMPLES

Example 1

Charge 50 g of FAME (SOYCLEAR™ 1500, available from AG Environmental Products, Inc.) and 5.8 g of formic acid (98-100% purity, obtained from RANKEM, RFCL Ltd.) to a 250-mL glass reactor equipped with an overhead stirrer having TEFLON™ blades and immersed in an oil bath having an initial temperature of 30° C. The amounts of FAME and formic acid employed achieve an acid-to-carbon/carbon double bond ("C=C") mole ratio of 0.5. Add 57.5 g of 30 vol % hydrogen peroxide ("$H_2O_2$") (obtained from Merck & Co.) solution (in water), resulting in an $H_2O_2$-to-C=C mole ratio of 2. Add the $H_2O_2$ at a continuous rate for the initial 2 hours; maintain reaction temperature at 40° C. by adjusting the temperature of the oil bath. Agitate the reaction mixture via the overhead stirrer at 400 rpm to ensure proper mixing in the reactor. Maintain the reaction conditions for a total of 11 hours, including feeding time. After 11 hours, stop the agitation and allow the reaction mixture to separate into aqueous (bottom) and organic (top) layers over 2 hours. Drain the resulting aqueous layer to separate most of the water and formic acid. Neutralize the organic layer with dilute sodium bicarbonate solution (0.1 M solution prepared by dissolving 8.4 g of sodium bicarbonate powder obtained from S.d. fine Chem in 1 liter of distilled water), which essentially removes residual formic acid. A total of 75 mL of 0.1 M sodium bicarbonate solution is added in 5 steps for neutralization. Thereafter, wash the organic layer with water, repeating until it becomes neutral (approximately 25 mL of water, total). Measure the pH of the wash water after each wash using pH paper; continue washing until it reaches a pH value of about 7. After the last wash, add 50 mL of distilled water to a separating funnel containing the organic layer. Shake the mixture to ensure adequate contact and allow the mixture to settle. Once separation is achieved, drain the bottom aqueous layer. Place the top organic layer under vacuum (~10 mbar (1,000 Pa), 60° C.) for two hours to remove residual water.

Example 2

Prepare an eFAME sample as described above in Example 1, except employ FAME prepared via transesterification of soybean oil as the starting material. Prepare FAME according to the following method. Charge 100 g (0.113 moles) of soybean oil (obtained from Cargill Gemini) to a 500-mL, 3-neck, round-bottom flask. Add 21.72 g (0.68 moles) of methanol (99.5% pure, obtained from Sigma Aldrich) to the reactor to maintain the mole ratio of methanol:soybean oil at 6:1. The reactor is equipped with a condenser, temperature sensor, and overhead stirrer having TEFLON™ blades. The reactor is immersed in an oil bath to maintain the reaction temperature at 60° C. under nitrogen flow. Once the reaction temperature of 60° C. is achieved, 4 g of 25% sodium methoxide dissolved in methanol (commercially available from Sigma Aldrich) is added to the reactor. After the reaction, wash the reaction mixture with water several times (till pH becomes about 7) to remove the residual sodium methoxide. Dry the final product under vacuum (10 mbar at 60° C.) to obtain FAME.

Example 3

Prepare an eFAME sample according to the method described in Example 1 using the starting material as prepared in Example 2, except maintain the epoxidation reaction temperature at 50° C. instead of 40° C.

Comparative Example 1

Prepare and eFAME sample by charging 50 g of FAME (as prepared in Example 2) and 5.8 g of formic acid to a glass reactor (acid-to-C═C mole ratio of 0.5) equipped as described in Example 1. Add 34.5 g of 50 vol % $H_2O_2$ (obtained from Merck) solution (in water), giving an $H_2O_2$-to-C═C mole ratio of 2, and at a continuous rate while agitating the reaction mixture and maintaining the reaction temperature between 60 and 70° C. After 6 hours of reaction time, stop the agitation and allow the reaction mixture to separate into aqueous and organic layers for 2 hours. The remaining steps are repeated as described in Example 1.

Comparative Example 2

Prepare and eFAME sample by charging 50 g of FAME (SOYCLEAR™ 1500) and 5.8 g of formic acid to a glass reactor (acid-to-C═C mole ratio of 0.5) equipped as described in Example 1. Add 34.5 g of 50 vol % $H_2O_2$ (obtained from Merck) solution (in water), giving an $H_2O_2$-to-C═C mole ratio of 2, and at a continuous rate while agitating the reaction mixture and maintaining the reaction temperature at 60° C. After 3 hours of reaction time, stop the agitation and allow the reaction mixture to separate into aqueous and organic layers for 2 hours. The remaining steps are repeated as described in Example 1.

Analyses

For each of the samples prepared as described above, determine the oxirane oxygen content according to the above-described procedure. Additionally, determine the iodine number for each sample according to the above-described procedure. Finally, determine the hydrophilic impurities content for each sample according to the above-described procedure. Results of these analyses are provided in Table 1, below.

TABLE 1

| Sample Properties | | | | | |
|---|---|---|---|---|---|
| Property | Ex. 1 | Ex. 2 | Ex. 3 | Comp. Ex. 1 | Comp. Ex. 2 |
| Oxirane oxygen (wt %) | 6.51 | 6.50 | 6.97 | 6.09 | 6.74 |
| Iodine number (g $I_2$/100 g) | 8.29 | 9.91 | 4.16 | 1.65 | 3.19 |
| Hydrophilic impurities (wt %) | 0.081 | 0.083 | 0.14 | 1.6 | 0.98 |
| Percent change in hydrophilic impurities relative to Comp. Ex. 2 | −92 | −92 | −86 | +64 | — |

As can be seen from the results in Table 1, the amount of hydrophilic impurities in eFAME Examples 1 and 2 was reduced by more than 90% when the iodine number was increased to between 8 and 10 from 3.2. The hydrophilic impurities content was also reduced by more than 85% when the iodine number was increased to above 4 from 3.2, as seen in Example 3. On the other hand, when the iodine number was decreased further to 1.6, hydrophilic impurities increased by more than 60%, as shown in Comparative Example 1.

The invention claimed is:
1. A plasticizer composition comprising:
epoxidized fatty acid alkyl esters,
wherein said epoxidized fatty acid alkyl esters have an iodine value in the range of from 7 to 10 g $I_2$/100 g of epoxidized fatty acid alkyl esters,
wherein said epoxidized fatty acid alkyl esters have an oxirane oxygen content of at least 6 weight percent based on the entire weight of the epoxidized fatty acid alkyl esters,
wherein said epoxidized fatty acid alkyl esters are prepared from esterified soybean oil,
wherein said epoxidized fatty acid alkyl esters have a hydrophilic impurities content of less than 0.8 weight percent based on the entire weight of said epoxidized fatty acid alkyl esters.
2. A polymeric composition comprising a polymeric resin and the plasticizer composition of claim 1.
3. The polymeric composition of claim 2, wherein said polymeric resin is a vinyl chloride resin, wherein said polymeric composition is an article of manufacture selected from the group consisting of blood bags, intravenous bags, saline solution bags, syringes, intravenous tubing, nasogastric tubing, catheter tubing, drainage tubing, examination gloves, oxygen masks, orthodontic retainers, artificial skin, and food packaging.
4. A process for producing epoxidized fatty acid alkyl esters, said process comprising:

epoxidizing fatty acid alkyl esters via controlled epoxidation by contact with an acid and an aqueous peroxide solution to form epoxidized fatty acid alkyl esters, wherein said controlled epoxidation comprises selecting a reaction temperature, a reaction time, an aqueous peroxide solution concentration, and a peroxide solution feed rate to cause said epoxidized fatty acid alkyl esters to retain sufficient unsaturation to present an iodine value in the range of from 7 to 10 g $I_2$/100 g of epoxidized fatty acid alkyl esters, wherein said epoxidized fatty acid alkyl esters have an oxirane oxygen content of at least 6 weight percent based on the entire weight of the epoxidized fatty acid alkyl esters, wherein said fatty acid alkyl esters are prepared by transesterifying a soybean oil, wherein said epoxidized fatty acid alkyl esters have a hydrophilic impurities content of less than 0.8 weight percent based on the entire weight of said epoxidized fatty acid alkyl esters.

5. The process of claim 4, wherein said reaction temperature is in the range of from 30 to 50° C., wherein said aqueous peroxide solution has a concentration of less than 40%, wherein said reaction time is greater than 6 hours, wherein said peroxide solution feed rate is in the range of from 0.3 to 4 moles of peroxide solution per molar equivalent of carbon-carbon double bonds in the fatty acid alkyl esters per hour.

6. The process of claim 4, wherein said epoxidized fatty acid alkyl esters have the structure: $R^1$—C(=O)O—$R^2$, wherein $R^1$ is a linear or branched $C_1$ to $C_8$ alkyl group, and $R^2$ represents saturated, mono-unsaturated, and/or polyunsaturated $C_{12}$ to $C_{22}$ epoxidized fatty acid chains.

* * * * *